US008883408B2

(12) United States Patent
Hamby et al.

(10) Patent No.: US 8,883,408 B2
(45) Date of Patent: *Nov. 11, 2014

(54) TISSUE IMPLANTS FOR IMPLANTATION AND METHODS OF PREPARING THE SAME

(71) Applicant: CryoLife, Inc., Kennesaw, GA (US)

(72) Inventors: Joseph Hamby, Woodstock, GA (US); Steven Walsh, Marietta, GA (US)

(73) Assignee: CryoLife, Inc., Kennesaw, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/754,029

(22) Filed: Jan. 30, 2013

(65) Prior Publication Data
US 2013/0142844 A1 Jun. 6, 2013

Related U.S. Application Data

(63) Continuation of application No. 12/831,053, filed on Jul. 6, 2010, now Pat. No. 8,377,143.

(51) Int. Cl.
A61L 27/36 (2006.01)

(52) U.S. Cl.
CPC ......... A61L 27/3687 (2013.01); A61L 2430/40 (2013.01); A61L 27/3604 (2013.01)
USPC ........................................ 435/1.3; 623/23.72

(58) Field of Classification Search
USPC ........................................ 435/1.3; 623/23.72
See application file for complete search history.

(56) References Cited

U.S. PATENT DOCUMENTS

| 4,695,536 | A | 9/1987 | Lindstrom et al. |
| 4,890,457 | A | 1/1990 | McNally et al. |
| 5,131,850 | A | 7/1992 | Brockbank |
| 5,145,769 | A | 9/1992 | McNally et al. |
| 5,158,867 | A | 10/1992 | McNally et al. |
| 5,160,313 | A | 11/1992 | Carpenter et al. |
| 5,171,660 | A | 12/1992 | Carpenter et al. |
| 5,333,626 | A | 8/1994 | Morse et al. |
| 5,460,962 | A | 10/1995 | Kemp |
| 5,730,933 | A | 3/1998 | Peterson |
| 5,741,782 | A | 4/1998 | Brockbank et al. |
| 5,866,539 | A | 2/1999 | Blackburn et al. |
| 5,899,936 | A | 5/1999 | Goldstein |
| 5,989,498 | A | 11/1999 | Odland |
| 6,206,931 | B1 | 3/2001 | Cook et al. |
| 6,908,591 | B2 | 6/2005 | MacPhee et al. |
| 7,129,035 | B2 | 10/2006 | Goldstein et al. |
| 7,318,998 | B2 | 1/2008 | Goldstein et al. |
| 7,658,706 | B2 | 2/2010 | Squillace |
| 7,723,108 | B2 | 5/2010 | Truncale et al. |
| 7,763,081 | B2 | 7/2010 | Ollerenshaw et al. |
| 7,763,459 | B2 | 7/2010 | Padmini et al. |
| 2001/0000804 | A1 | 5/2001 | Goldstein et al. |
| 2003/0087428 | A1* | 5/2003 | Wolfinbarger et al. ....... 435/325 |
| 2003/0228300 | A1 | 12/2003 | Haspel et al. |
| 2003/0228692 | A1 | 12/2003 | Goldstein et al. |
| 2004/0161362 | A1 | 8/2004 | Bogert |
| 2005/0229323 | A1* | 10/2005 | Mills et al. ...................... 8/94.11 |
| 2006/0275377 | A1 | 12/2006 | Gomes et al. |
| 2008/0077251 | A1 | 3/2008 | Chen et al. |
| 2008/0306610 | A1 | 12/2008 | Wang et al. |
| 2009/0017439 | A1 | 1/2009 | Shimko et al. |
| 2010/0285587 | A1 | 11/2010 | Ollerenshaw et al. |
| 2012/0259415 | A1 | 10/2012 | Van Dyke et al. |

FOREIGN PATENT DOCUMENTS

WO 9212632 A1 8/1992

OTHER PUBLICATIONS

Muthusami et al.; Mycobacterium fortuitum: an iatrogenic cause of soft tissue infection in surgery; ANZ Journal of Surgery; vol. 74; No. 8; pp. 662-666; published Aug. 2004.*
Angell, William W., et al., "Durability of the viable aortic allograft," J. Thorac Cardiovasc Surg (1989) 98:48-56.
Armiger, Lois C., et al., "Histological Assessment of Orthotopic Aortic Valve Leaflet Allografts: Its Role in Selecting Graft Pre-Treatment," Pathology (1983), vol. 15, pp. 67-73.
Breukink, Eefjan, et al., "Lipid II is an intrinsic component of the pore induced by nisin in bacterial membranes," JBC Papers in Press. Published on Mar. 26, 2003 as Manuscript M301463200.
Brumfitt, W., et al., "Nisin, alone and combined with peptidoglycan-modulating antibiotics: activity against methicillin-resistant Staphylococcus aureus and vancomycin-resistant enterococci," Journal of Antimicrobial Chemotherapy (2002) 50, 731-734.
Carneiro De Melo, Alexandra M. S., et al., "Nisin Stimulates Oxygen Consumption by Staphylococcus aureus and Escherichia coli," Applied and Environmental Microbiology, May 1996, pp. 1831-1834.
Dawson, Michael John, "Lantibiotics as antimicrobial agents," Expert Opin. Ther. Patents (2007) 17(4), pp. 365-369.
Deibel, Virginia, et al., "The Clean Operation: Biofilms: Forming a Defense Strategy for the Food Plant," bio-reveal—Real-time Microbial Detection System (http://www.bio-reveal.com/food_biofilms-en.html), Apr. 21, 2009.
Di Giulio, Antonio, et al., "Antimicrobial Peptides: Basic Mechanism of Action and Emerging Pharmacological Interest," Asian Journal of Biochemistry 1 (1):28-40, 2006.
Donlan, Rodney M., "Biofilms and Device-Associated Infections," Centers for Disease Control and Prevention, Atlanta, GA, USA, Emerging Infections Diseases, vol. 7, No. 2, Mar.-Apr. 2001, pp. 277-281.
Giacometti, A., et al., "In-vitro activity and killing effect of polycationic peptides on methicillin-resistant Staphylococcus aureus and interactions with clinically used antibiotics," Diagn Microbiol Infect Dis. Oct. 2000; 38 (2):115-8 [Abstract].
Goldstein, Beth P., et al., "Activity of nisin against Streptococcus pneumoniae, in vitro, and in a mouse infection model," J. Antimicrob Chemother 1998; 42:277-278.

(Continued)

Primary Examiner — Jim Ketter
Assistant Examiner — Antonio Galisteo Gonzalez
(74) Attorney, Agent, or Firm — Sutherland Asbill & Brennan LLP

(57) ABSTRACT

A method is provided for preparing a tissue implant for implantation. The method includes harvesting a tissue material from a human or an animal donor, treating the tissue material in a nuclease-containing solution, and thereafter treating the tissue material with an alkaline alcohol solution. The nuclease-containing solution includes an antimicrobial. The alkaline alcohol solution comprises sodium hydroxide and ethanol.

20 Claims, 7 Drawing Sheets

(56) References Cited

OTHER PUBLICATIONS

Gut, Ian M., et al., "Inhibition of *Bacillus anthracis* Spore Outgrowth by Nisin," Antimicrobial Agents and Chemotherapy, Dec. 2008, vol. 52, No. 12, pp. 4281-4288.

Hawley, H. B., et al., "The Development and Use of Nisin," (Symposium on Recent Advances in the Bacteriology of Milk and Mil Products: Paper V), Journal of Applied Microbiology, vol. 18, No. 2, pp. 388-395, 1955, Aplin & Barrett, Ltd., Yeovil, Somerset.

Heacox, A. E., et al., "Factors affecting the viability of cryopreserved allograft heart valves," Cardiac Valve Allografts: 1962-1987, CryoLife, Inc., Marietta, USA, pp. 37-42, ISBN 3-7985-0754-6 (Steinkopff) Gb, 1988.

Kirklin, John W., et al., "Cardiac Surgery," A Wiley Medical Publication, 1986, Chapter 12, Aortic Valve Disease, pp. 421-422, ISBN 0-471-01416-8.

Lactoferrin (http://en.wikipedia.org/wiki/Lactoferrin), Apr. 18, 2007.

Lange, Perry L., et al., "Allograft Valve Banking: Techniques and Technology," Cardiac Reconstructions with Allograft Valves, 1989, ISBN 0-387-96855-5, Springer-Verlag, New York, Berlin, Heidelberg.

Liu, Wei, et al., "Some Chemical and Physical Properties of Nisin, a Small Protein Antibiotic Produced by *Lactococcus lactis*," Applied and Environmental Microbiology, Aug. 1990, pp. 2551-2558.

Lysozyme (http://en.wikipedia.org/wiki/Lysozyme), Apr. 18, 2007.

Mahdavi, M., et al., "The effect of nisin on biofilm forming foodborne bacteria using microtiter plate method," Research in Pharmaceutical Sciences, Oct. 2007; 2(2):113-118.

Maher, Sam, et al., "Investigation of the cytotoxicity of eukaryotic and prokaryotic antimicrobial peptides in intestinal epithelial cells in vitro," Biochemical Pharmacology, vol. 71, Issue 9, Apr. 28, 2006, pp. 1289-1298. [Abstract].

Mota-Meira, Marilaine, et al., "MICs of Mutacin B-Ny266, Nisin A, Vancomycin, and Oxacillin against Bacterial Pathogens," Antimicrobial Agents and Chemotherapy, Jan. 2000, pp. 24-29.

Nisin (http://en.wikipedia.org/wiki/Nisin), Apr. 18, 2007.

Nomura, Masaru, et al., "Novel characteristic for distinguishing *Lactococcus lactis* subsp. Lactis from subsp. cremoris," International Journal of Systematic Bacteriology (1999), 49, 163-166.

Olitsky, Peter K., "Physical, Chemical, and Biological Studies on the Virus of Vesicular Stomatitis of Horses—Comparison with the Virus of Foot-and-Mouth Disease," (From the Laboratories of the Rockefeller Institute for Medical Research.) (Published Jun. 1, 1927), pp. 969-981.

Olson, Merle E., et al., "Biofilm bacteria: formation and comparative susceptibility to antibiotics," The Canadian Journal of Veterinary Research, 2002; 66:86-92.

Pongtharangkul, T., et al., "Evaluation of agar diffusion bioassay for nisin quantification," Appl Microbiol Biotechnol (2004) 65:268-272.

Reddy, K.V. R., et al., "Evaluation of antimicrobial peptide nisin as a safe vaginal contraceptive agent in rabbits; in vitro and in vivo studies," Reproduction (2004) 128:117-126.

Richter, Edward, "Re: What is Nisin and what does it do in terms of food preservation," MadSci Network: Microbiology, Posted May 8, 2001 (http://www.madsci.org/posts/archives/jun2001/99209382.Mi.r.html).

Savadogo, Aly, et al., "Bacteriocins and lactic acid bacteria—a minireview," African Journal of Biotechnology, May 2, 2006, vol. 5 (9), pp. 678-683.

Strickett, Marianne G., et al., "Disinfection of Human Heart Valve Allografts with Antibiotics in Low Concentration," Pathology (1983), vol. 15, pp. 457-462.

Tramer, J., et al., "Estimation of Nisin in Foods," J. Sci. Fd. Agric., 1964, vol. 15, August, pp. 522-528.

Valenta, C., et al., "The antistaphylococcal effect of nisin in a suitable vehicle: a potential therapy for atopic dermatitis in man," J. Pharma Pharmacol. Sep. 1996; 48(9):988-91. [Abstract].

Wang, Xiaohong, et al., "Effect of nisin on the growth of *Staphylococcus aureus* determined by a microcalorimetric method," Mol. Nutr. Food Res. 2005, 49, pp. 350-354.

Watts, Lesley K., et al., "Establishment of a Viable Homograft Cardiac Valve Bank: A Rapid Method of Determining Homograft Viability," The Annals of Thoracic Surgery, vol. 21, No. 3, Mar. 1976, pp. 230-236.

Wiedemann, Imke, et al., "Lipid II-Mediated Pore Formation by the Peptide Antibiotic Nisin: a Black Lipid Membrane Study," Journal of Bacteriology, May 2004, pp. 3259-3261.

Bellows, Charles, et al., "Abdominal Wall Reconstruction Using Biological Tissue Grafts: Present Status and Future Opportunities," Future Drugs, Expert Rev. Med. Devices 3(5), 2006, pp. 657-675.

Harding, Keith, et al., "Acellular Matrices for the Treatment of Wound Healing. An Expert Working Group Review" London: Wounds International 2010.

Pruss, A, et al., "Paracetic Acid-ethanol Treatment of Allogeneic Avital Bone Tissue Transplants—A Reliable Sterilization Method," Ann Transplant, 2003; 8(2):34-42.

Gupta, et al., Development of a Multidose Formulation for a Humanized Monoclonal Antibody Using Experimental Design Techniques; AAPS PharmSci; vol. 5 (2); pp. 1-9; published Apr. 4, 2003.

"Tissue," Merriam-Webster.com, accessed Jun. 13, 2012.

\* cited by examiner

TISSUE IMPLANTS FOR IMPLANTATION AND METHODS OF PREPARING THE SAME

CROSS-REFERENCE TO RELATED APPLICATIONS

The present application is a continuation of U.S. application Ser. No. 12/831,053, filed Jul. 6, 2010, which is incorporated by reference herein in its entirety.

FIELD OF THE INVENTION

This invention is generally in field of tissue implants for implantation and methods for preparing the same. More specifically, the present invention generally relates to decellularized tissue implants, methods for preparing decellularized tissue implants for implantation, and method of using the decellularized tissue implants.

BACKGROUND

Decellularized tissue implants have many potential applications in reconstructive and rehabilitative procedures. For example, decellularized tissues implant may be used to reinforce soft tissues where weakness exists, to reconstruct damaged or defective tissue structures, and/or to patch holes or defects in tissue surfaces. Decellularized tissue implants are generally sought having such properties as suitable tensile, burst, and suture retention strength; biocompatibility; low risk of pathogen transmission and the ability to support recellularization in vivo. It therefore would be desirable to provide improved tissue implants having the desired properties, and, in particular, it would be desirable to provide new and improved methods for preparing decellularized tissues and tissue implants.

SUMMARY

In one aspect, a method is provided for preparing a tissue implant for implantation. The method includes treating a tissue material in a nuclease-containing solution, and treating the tissue material with an alkaline alcohol solution. The nuclease-containing solution includes an antimicrobial.

In another aspect, a method is provided for preparing a tissue implant for implantation. The method includes treating a tissue material in a nuclease-containing solution that includes benzyl alcohol.

In another aspect, a method is provided for preparing a tissue implant for implantation. The method includes treating a decellularized tissue material with an alkaline alcohol solution.

In yet another aspect, a method is provided for preparing a tissue implant for implantation. The method includes harvesting a tissue material from a human or an animal donor, treating the tissue material in a nuclease-containing solution, and thereafter treating the tissue material with an alkaline alcohol solution. The nuclease-containing solution includes an antimicrobial. The alkaline alcohol solution comprises sodium hydroxide and ethanol.

DETAILED DESCRIPTION

New methods of producing tissue implants have been developed. These methods may be used to produce tissue implants for implantation having beneficial properties, e.g., suitable tensile, burst, and suture retention strength; biocompatibility; low risk of pathogen transmission and the ability to support recellularization in vivo.

In particular, new methods are provided for reducing or preventing the growth of bacteria and inactivating viruses when preparing a tissue implant, such as decellularized tissue implant, for implantation. Such methods also may produce decellularized tissue implants having desirable textural qualities that allow for improved handling of the tissue implant, such as when implanting the tissue implant during a surgical procedure. Such objectives may be achieved by treating a tissue material in a nuclease-containing solution that comprises an antimicrobial; and treating the tissue material with an alkaline alcohol solution.

The methods may be used to produce decellularized tissue implants from xenograft or allograft tissues, including but not limited to vascular tissues, orthopedic tissues, connective tissues, cardiac tissues, and other tissues that are sheet-like in configuration, such as peritoneum, pericardium, diaphragmatic ligament, fascia lata, urinary bladder, omentum, skin, and dermis. In one embodiment, pericardium is harvested from a bovine donor and then processed as described herein to form a decellularized tissue implant, which subsequently is implanted in a human patient in need thereof.

I. Methods

New methods have been developed for preparing tissue implants for implantation, particularly decellularized tissue implants. In an exemplary embodiment, the method may include obtaining a starting tissue material, lysing cells within the starting tissue in a hypotonic solution, treating the tissue in a solution comprising a nuclease and antimicrobial such as benzyl alcohol, treating the tissue with an alkaline alcohol, treating the tissue with chlorine dioxide, treating the tissue with an antioxidant, and vacuum sealing the tissue in a package. The tissue implant may be thereafter frozen and/or sterilized by ionizing radiation. Alternatively, in some embodiments, the tissue implant may be chemically sterilized prior to packaging or after packaging, e.g., prior to vacuum sealing. The tissue implant may be stored cryopreserved, frozen, refrigerated, or at ambient temperature storage conditions depending on the final configuration of the tissue implant.

Figure 1:
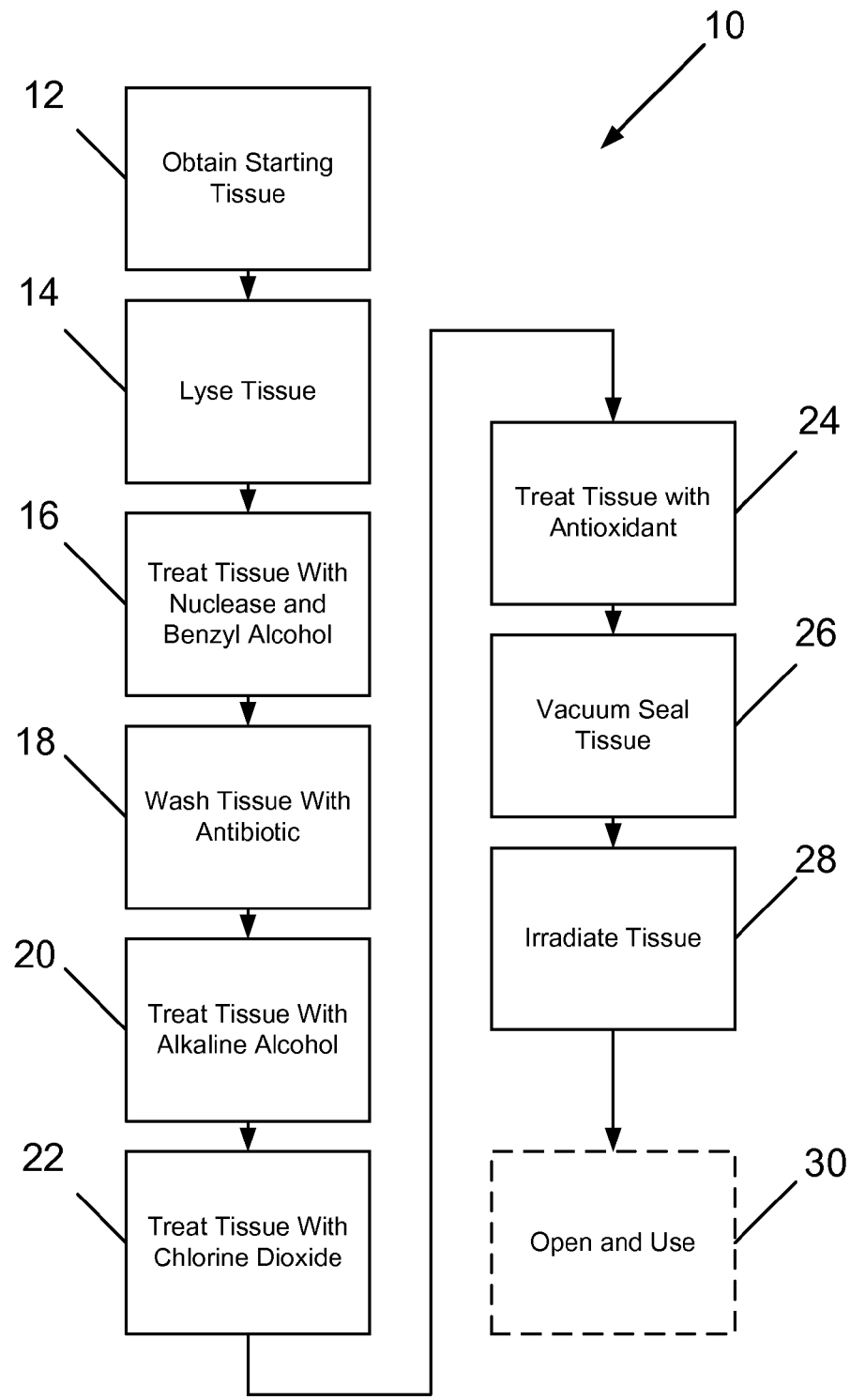
FIG. 1 is a schematic, illustrating a method of preparing a tissue implant for implantation in accordance with one or more embodiments of the present invention.

For example, as illustrated in FIG. 1, an exemplary method 10 for preparing a tissue implant for implantation may comprise a series of treatment steps that transform a harvested, starting tissue material into a tissue implant, which may be implanted in a patient for various purposes, particular therapeutic, prophylactic, reconstructive, or other medical purposes. Initially, a starting tissue material may be obtained in accordance with step 12. The starting tissue material may be harvested from a variety of animal donor tissues, including human or other mammalian sources. For example, a portion of bovine pericardium may be acquired. The starting tissue material may then be lysed in a hypotonic solution in accordance with step 14. The step of lysing the tissue may cause the cells of the starting tissue to osmotically rupture or otherwise render the cells susceptible to decellularization by subsequent processing steps. The tissue may then be treated with a solution comprising a nuclease and benzyl alcohol to eliminate or reduce the content of DNA and/or RNA present in the tissue in accordance with step 16. The tissue may then be washed with an antibiotic solution in accordance with step 18, which may also aid in removing cellular remnants and debris from the tissue. The tissue may then be treated with an alkaline alcohol solution in accordance with step 20. The alkaline alcohol treatment may change the texture of the tissue material, providing tactile qualities that make it easier to handle during surgery. Thereafter, the tissue may be treated with a solution comprising chlorine dioxide in accordance with step 22. The tissue may then be subjected to an antioxidant treatment in accordance with step 24. For example, the tissue may be submerged in a solution comprising ascorbic acid or a salt thereof, e.g., sodium ascorbate. The tissue may then be vacuum sealed in a package in accordance with step 26. In certain embodiments, the tissue implant is vacuum sealed in the antioxidant treatment solution. The tissue may then be irradiated with gamma or electron beam radiation in accordance with step 28. The tissue implant may then be removed from the package and used in accordance with step 30.

Various uses of the tissue implant are contemplated. For example, the tissue implant may be implanted and sutured to a patient to perform a reconstructive or reinforcing function. For instance, the tissue implant may be implanted to reinforce soft tissues where weakness exists, including but not limited to defects of the abdominal and thoracic wall, muscle flap reinforcement, rectal and vaginal prolapse, reconstruction of the pelvic floor, hernias, suture line reinforcement, reconstructive procedures, and urinary procedures. In another example, the tissue implant may be implanted for reinforcement of soft tissues repaired by sutures or by suture anchors during tendon repair surgery, including reinforcement of rotator cuff, patella, Achilles, bicep, quadriceps, or other tendon or ligament.

Figure 2:
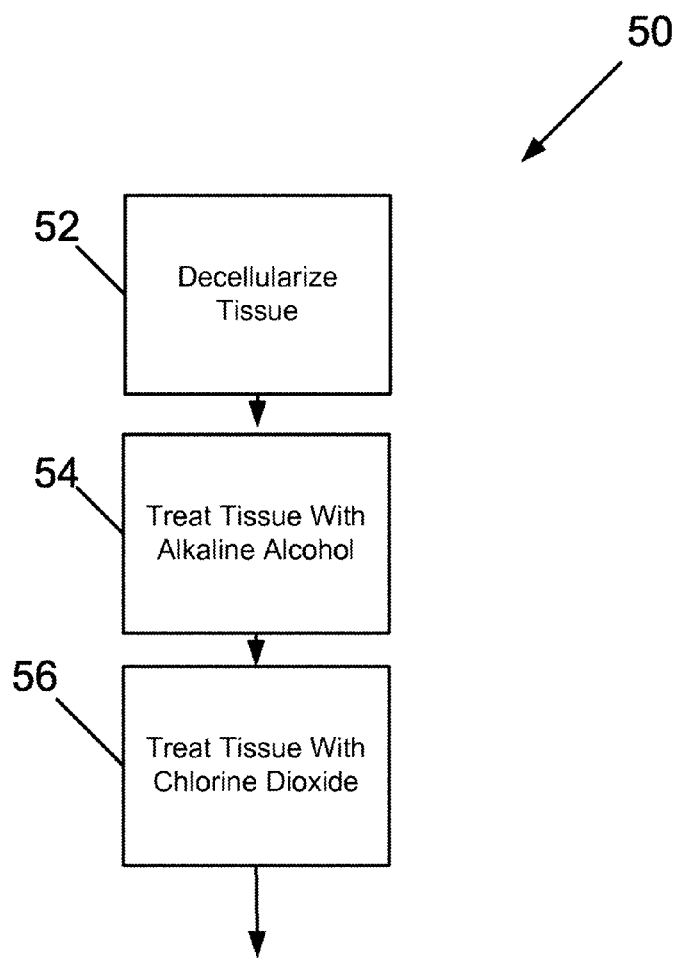
FIG. 2 is a schematic, illustrating a method of preparing a tissue implant for implantation in accordance with one or more embodiments of the present invention.

In some embodiments, a tissue implant is prepared for implantation by decellularizing a starting tissue material, treating the tissue with an alkaline alcohol, and treating the tissue with chlorine dioxide. For example, an exemplary method 50 for preparing a tissue implant for implantation is illustrated in FIG. 2. Initially, a starting tissue material may be decellularized in accordance with step 52. Various methods may be employed to decellularize the starting tissue material, such as hypotonic lysing, treatment with a nuclease, and/or treatment with a detergent. The tissue material may thereafter be treated with an alkaline alcohol solution in accordance with step 54. For example, the tissue may be treated with a solution comprising ethanol and sodium hydroxide. The tissue may thereafter be treated with chlorine dioxide in accordance with step 56.

Figure 3:
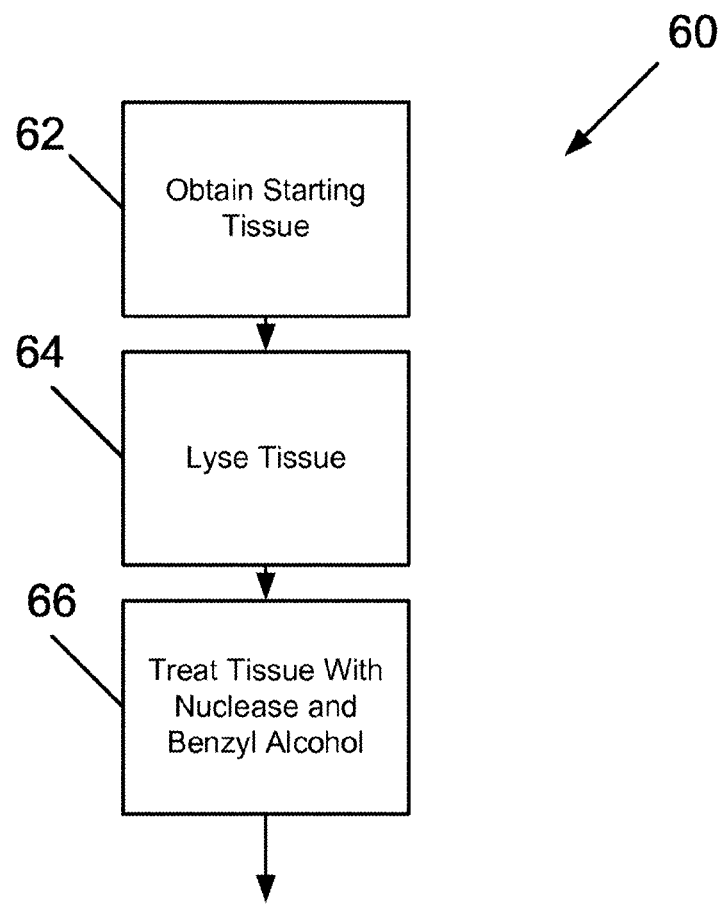
FIG. 3 is a schematic, illustrating a method of preparing a tissue implant for implantation in accordance with one or more embodiments of the present invention.

In some embodiments, a tissue implant is prepared for implantation by obtaining a starting tissue material, lysing the starting tissue, and treating the tissue in a solution comprising a nuclease and an antimicrobial agent, such as a preservative, for example, benzyl alcohol. An exemplary method 60 for preparing a tissue implant for implantation is illustrated in FIG. 3. Initially, a starting tissue material may be obtained in accordance with step 62. The starting tissue material may thereafter be lysed in accordance with step 64. For example, the starting tissue material may be lysed in water or a hypotonic or other solution effective to initiate cell lysis. The tissue may thereafter be treated with a solution comprising a nuclease and an antimicrobial, such as benzyl alcohol, in accordance with step 66. For example, the solution may comprise a DNase and/or an RNase or other endonuclease that is reactive with DNA and/or RNA. The benzyl alcohol may be present in a concentration of about 0.8% to about 2.0% (v/v).

Figure 4:
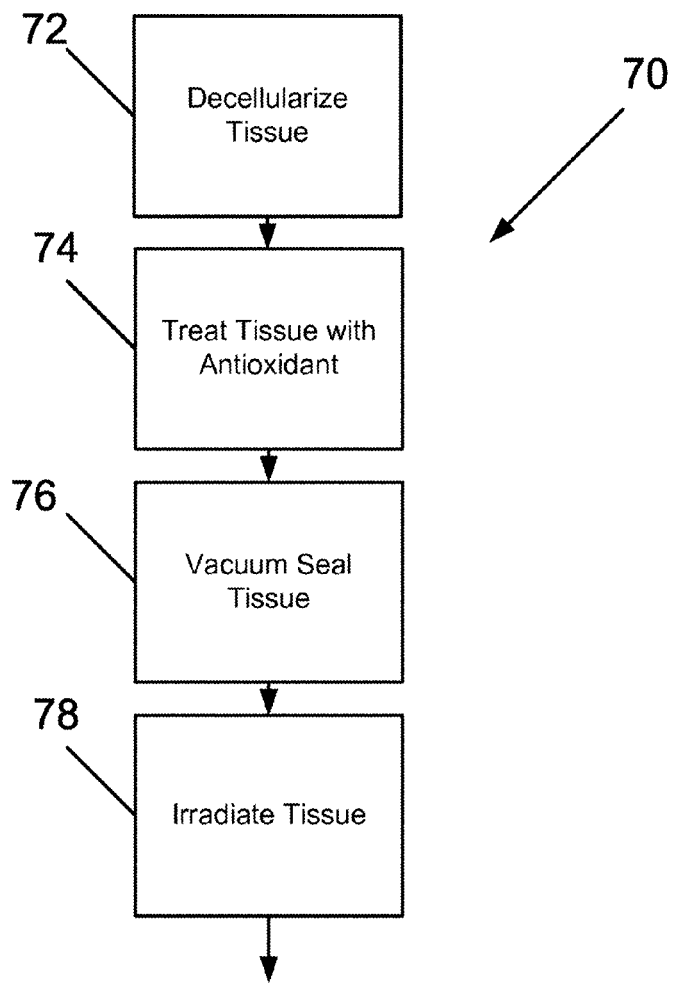
FIG. 4 is a schematic, illustrating a method of preparing a tissue implant for implantation in accordance with one or more embodiments of the present invention.

In some embodiments, a tissue implant is prepared for implantation by decellularizing a starting tissue material, treating the tissue with an antioxidant, vacuum sealing the tissue in a package, and irradiating the tissue. For example, an exemplary method 60 for preparing a tissue implant for implantation is illustrated in FIG. 4. Initially, a starting tissue material may be decellularized in accordance with step 72. The decellularized tissue may then be treated with an antioxidant in accordance with step 74, and vacuum sealed in the package with the antioxidant in accordance with step 76. The tissue may thereafter be irradiated for terminal sterilization in accordance with step 78.

Figure 5:
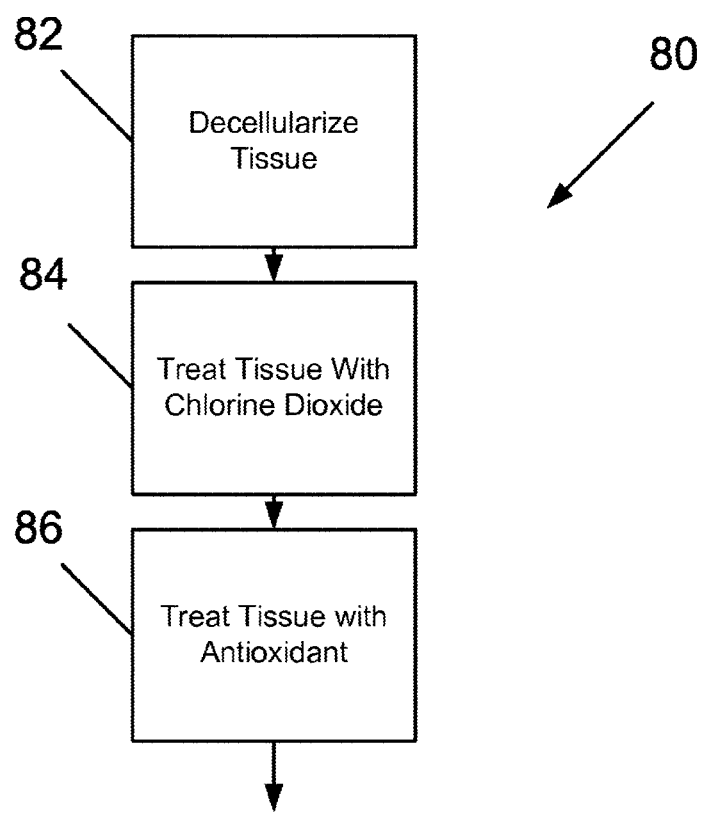
FIG. 5 is a schematic, illustrating a method of preparing a tissue implant for implantation in accordance with one or more embodiments of the present invention.

In some embodiments, a tissue implant is prepared by decellularizing a starting tissue material, treating the tissue material with chlorine dioxide, and treating the tissue with an antioxidant. For example, an exemplary method 80 for preparing a tissue implant for implantation is illustrated in FIG. 5. Initially, a starting tissue material may be decellularized in accordance with step 82. The decellularized tissue may then be treated with chlorine dioxide in accordance with step 84. For example, the tissue may be treated with a solution comprising 130 ppm chlorine dioxide in phosphate-buffered saline at a refrigerated temperature. The tissue may thereafter be treated with an antioxidant, such as ascorbic acid or a salt form thereof, in accordance with step 86. For example, the tissue may be treated with a solution comprising about 9.0 mM to about 11.0 mM sodium ascorbate in phosphate-buffered saline.

In another embodiment, the method may include harvesting tissue from a tissue donor and immediately rinsing the tissue with water or a hypotonic solution effective to initiate cellular lysis. The harvested tissue thereafter may be treated with a solution comprising a nuclease and an antimicrobial, such as a preservative, for example, benzyl alcohol. The tissue is thereafter treated with an alkaline alcohol, and then treated with a solution comprising chlorine dioxide. The tissue is then treated with an antioxidant, vacuum sealed in a package, and irradiated with ionizing radiation while in the package. Advantageously, this process may achieve effective sterilization without the use of antibiotics or the use of phosphate-buffered solution in procurement. Such a method may also increase process efficiency by reducing production time and cost.

Figure 6:
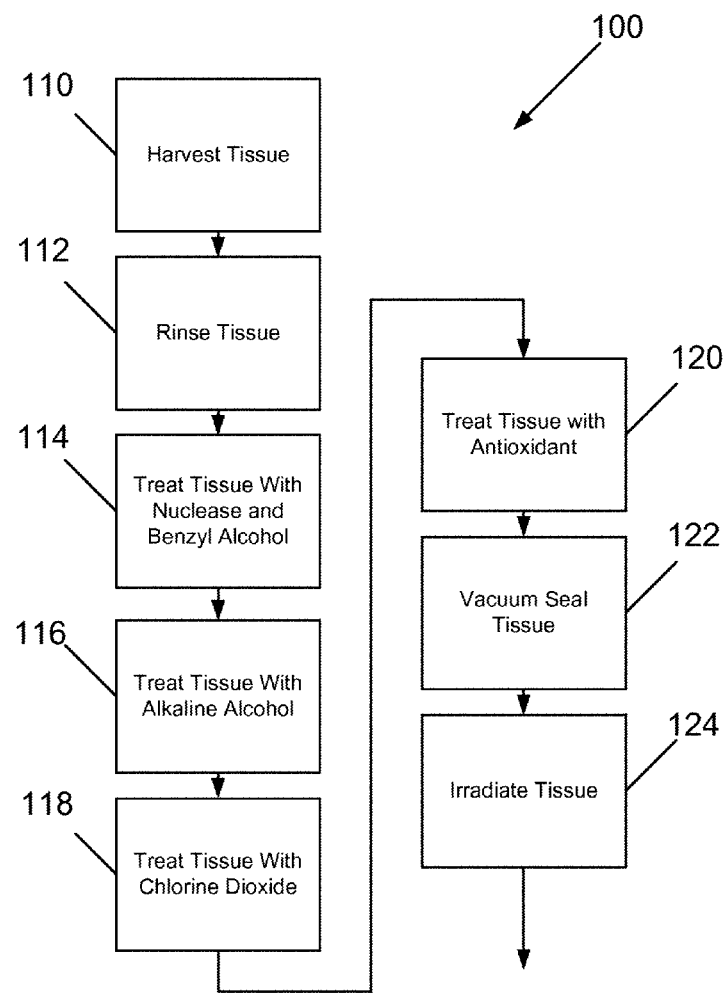
FIG. 6 is a schematic, illustrating a method of preparing a tissue implant for implantation in accordance with one or more embodiments of the present invention.

An exemplary antibiotic-free process 100 is illustrated in FIG. 6. Initially, tissue is harvested from a human or non-human donor in accordance with step 110. The tissue is then immediately treated with water to initiate cellular lysis in accordance with step 112. The tissue may be maintained in the water for a sufficient period of time to osmotically rupture the cells or otherwise render the tissue susceptible to decellularization by later processing steps. For example, the tissue may be transported in water from the harvest site to a site where the tissue will be prepared into a tissue implant, maintaining the tissue in hypotonic conditions during the period of transport. The tissue may thereafter be treated in a nuclease solution in accordance with step 114. The nuclease solution may comprise an antimicrobial, such as benzyl alcohol in an amount sufficient to prevent the growth of bioburden during nuclease treatment. The tissue may then be treated with an alkaline alcohol solution in accordance with step 116. For example, the tissue may be treated in a solution comprising ethanol and sodium hydroxide. The ethanol may be present in a concentration of about 72% to about 88% (v/v). The solution may comprise about 0.016 M to about 0.022 M sodium hydroxide. The tissue may then be treated with chlorine dioxide in accordance with step 118. For example, the tissue may be treated with a solution comprising 130 ppm chlorine dioxide in phosphate-buffered saline at a refrigerated temperature. The tissue may thereafter be treated with an antioxidant, such as ascorbic acid or a salt form thereof, in accordance with step 120. For example, the tissue may be treated with a solution comprising about 9.0 mM to about 11.0 mM sodium ascorbate in phosphate-buffered saline. The tissue may thereafter be vacuum sealed in a package in accordance with step 122, and irradiated for terminal sterilization using ionizing radiation in accordance with step 124.

Figure 7:
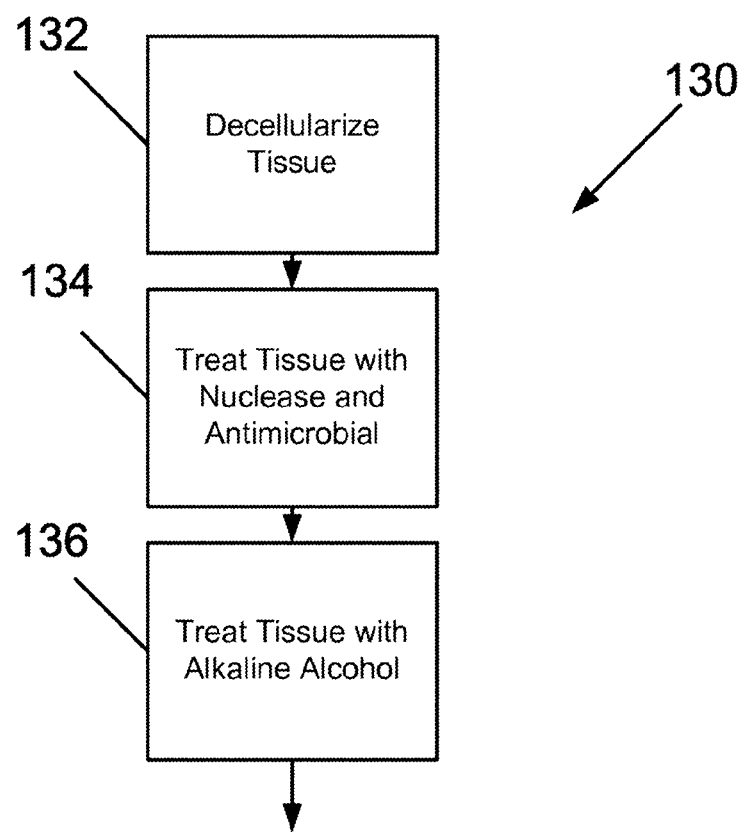
FIG. 7 is a schematic, illustrating a method of preparing a tissue implant for implantation in accordance with one or more embodiments of the present invention.

In some embodiments, a tissue implant may be prepared for implantation by treating a tissue material in a nuclease-containing solution, the nuclease-containing solution comprising an antimicrobial; and thereafter treating the tissue material with an alkaline alcohol solution. For example, an exemplary tissue treatment method 130 is illustrated in FIG. 7. The tissue may be decellularized, such as by lysing the native cells of the tissue, treating the tissue with a nuclease and/or treating the tissue with a detergent, in accordance with step 132. The tissue may then be treated with a nuclease solution that comprises an antimicrobial in accordance with step 132. For example, the nuclease solution may comprise a preservative, such as benzyl alcohol in an amount sufficient to prevent the growth of bioburden during nuclease treatment. The tissue may then be treated with an alkaline alcohol in accordance with step 134.

In some embodiments, the methods described herein are performed by moving the tissue material between different containers that contain the various treatment solutions. In other embodiments, the methods described herein are performed by maintaining the tissue material in a container, and serially filling the container with a series of treatment solutions. For example, the various treatment solutions may be circulated through the container sequentially. In some embodiments, the container is filled with a treatment solution, then the container is drained, and a second treatment solution is added. In some embodiments, the methods are performed by a combination of the foregoing. Moreover, one or more steps of the process may be partially or totally automated. To facilitate such processes, the tissue may be secured to a tissue holding device to ensure uniform exposure of the tissue to the treatment solution. For example, the tissue may be attached to a frame. The frame may maintain the tissue in a plane so that the tissue does not fold during treatment.

It is contemplated that methods of preparing tissue implants for implantation may comprise various combinations of the foregoing steps consistent with the teachings of the present disclosure. For example, steps of the method of FIG. 3 may be combined with the steps of any of the methods of FIG. 2, FIG. 4, FIG. 5, and/or FIG. 7. Furthermore, although the present methods are described in the context of unfixed allograft and xenograft tissue materials, aspects of the disclosed methods may also be utilized with biosynthetic material and/or fixed biologics. That is, the source tissues may be produced using in vitro tissue synthesis techniques as well as recombinant means known in the art. For example, the described alkaline alcohol, chlorine dioxide, and ascorbate treatment solutions may be used in antiviral and sterilization treatment processes for biosynthetic and fixed tissues. In addition, treatment with a nuclease may be omitted in some embodiments, particularly in non-cardiac applications. Other variations would be obvious to one of ordinary skill in the art in view of the present disclosure. Various steps for preparing a tissue implant for implantation are described in greater detail below.

A. Tissue Procurement

Biological tissues suitable for use in the present methods include those appropriate for implantation into humans or animals. Biological tissue for transplantation may be harvested from various sources. Tissues can be human or non-human, e.g., bovine, porcine, equine, ovine, macropodidae (e.g., kangaroo) or non-human primate in origin. Such starting tissue materials include tissue materials that are derived from human or -nonhuman sources. The present methods may be used to prepare allograft or xenograft tissue for implantation in humans.

While the present invention is often exemplified by reference to pericardium, particularly bovine pericardium, the present methods are applicable to other tissues as well, particularly soft tissues. Specifically, the present methods may be employed to prepare connective tissue, muscle tissue, nervous tissue or epithelial tissue for implantation. Examples of suitable epithelial, mesothelial, and endothelial tissues include skin tissues and the tissues that line body cavities and lumen, including, but not limited to, pericardium, peritoneum, pleura, blood vessels (e.g., veins and arteries), stomach, intestines, esophagus, Fallopian tubes, endometrium, cervix, vagina, trachea, bronchioles, tympanic membrane, ureter, umbilical cord and bladder. Other tissues that may be used include tendons, ligaments, fascia, dura mater, diaphragm, and heart valves.

In an exemplary embodiment, the biological tissue comprises bovine pericardium. The pericardial sac may be sourced and harvested in accordance with applicable regulatory requirements. The tissue may be thereafter transported in a suitable physiological buffer solution. For example, the tissue may be transported in phosphate-buffered saline (PBS) in refrigerated conditions.

In another embodiment, the tissue material may be harvested from a human or non-human donor and then treated with water, e.g., deionized water or a hypotonic solution, to initiate cellular lysis. In some embodiments, the tissue material is treated with deionized water or a hypotonic solution multiple times to serially reduce the intrinsic bioburden and initiate cellular lysis. In certain embodiments, the treatment solution may comprise antibiotics to provide active bioburden reduction. The treatment solution may comprise antimicrobial or bacteriostatic agents, e.g., benzyl alcohol, to reduce the potential for bacterial outgrowth. The treatment solution may also include an alkaline alcohol, e.g., sodium hydroxide and ethanol, to reduce bioburden and viral content. The treatment solution may also include one or more surfactants. In yet another embodiment, the treatment solution may be a hypertonic solution and the tissue material may be later treated with a hypotonic solution, e.g., during shipping.

The material may then be packaged in a container for shipping and maintained frozen, cold, or at ambient temperature during transport. In some embodiments, the tissue material may be maintained in water under hypotonic and refrigerated conditions during transport from the harvest site. The shipping solution may also include antibiotics and or bacteriostatic agents, such as benzyl alcohol. Preferably, the tissue material is maintained between ambient and freezing temperature during the entire procurement process to reduce biochemical degradation and bacterial blooms. Alternatively, the tissue may be dried, flash frozen, and then shipped in a frozen state without using a shipping solution.

B. Tissue Dissection

Before subjecting the tissue to the decellularization and treatment methods described herein, the tissue may be trimmed to a desired size and shape. Before trimming the tissue, a portion of the tissue may be first selected that has desired thickness and physical properties and is generally free from defects. The selected portion of the tissue may be cut to the desired shape and size. For example, a patch may be cut from the tissue in the shape of a circle, ellipse, oval, or rectangle. In a preferred embodiment, the tissue may be cut in a substantially circular shape, for example, a circle having a diameter of about 4 cm to about 12 cm, or more preferably about 5 cm to about 10 cm, or about 7 cm. In another embodiment, the tissue may be cut to form a patch that is substantially elliptical in shape, such as a 5 cm by 8 cm ellipse. Other shapes may be used including regular and irregular polygons, curvilinear shapes, and combinations thereof.

In some embodiments, a portion of pericardium may be selected that is free of non-target or non-desired tissue elements and is substantially uniform in thickness. For bovine pericardium, it is generally possible to cut a 10 cm by a 20 cm rectangular sheet from the pericardial sac that is free of extraneous connective tissue and substantially uniform in thickness. In one embodiment, the entire sheet is subjected to the decelluralization and treatment methods described herein. In other embodiments, the sheet is cut into smaller portions, e.g., patches, before being subjected to the decelluralization and treatment methods described herein.

In some embodiments, the tissue is cut with a laser. In certain embodiments, the laser is computer-controlled to cut the desired shape based on a computer program. The controller may automatically adjust the direction, power, and speed of the laser and/or automatically adjust the orientation or location of the tissue relative to the laser. Laser cutting may result in a Heat Affected Zone (HAZ) at the edge of the cut. In some embodiments, the HAZ may be removed by washing the tissue in a solution, such as sodium ascorbate. In some embodiments, HAZ is avoided or minimized by using an ultra fast laser, i.e., a laser with a short pulse duration, such as a femtosecond laser. In other embodiments, the tissue may be cut using a high-velocity water stream, an arc cutter, a clicker press, or manually with a bladed instrument.

Other biological tissues may be trimmed to form patches and/or other tissue articles of various shapes and sizes. The specific shape and size will depend on the intended use of the patch or article.

C. Hypotonic Lysis

The trimmed tissue may then be placed in hypotonic solution in order to effect cell lysis. When placed in a hypotonic solution water may be drawn into the cells of the tissue through the cell membrane via osmosis. This may cause the cells of the tissue to swell and burst. In some embodiments, the tissue may be retained in the hypotonic solution for a period of time sufficient to cause the cells of the starting tissue to osmotically rupture or otherwise render the cells susceptible to decellularization by subsequent processing steps. The term "decellularization" as used herein refers to the destruction of the cells of a tissue material. Various observational and/or quantitative methods are known for evaluating decellularization and measuring the degree thereof. For example, the degree of decellularization may be measured by performing a hematoxylin stain of nuclei present in a starting tissue and the processed tissue and comparing the results. A tissue may be considered "essentially acellular" if the tissue comprises at least 70% fewer hematoxylin stainings than the starting cellular tissue material. More preferably, a decellularized tissue comprises 95% fewer, or even more preferably 99% fewer hematoxylin stainings than the starting cellular tissue material.

Solutions for effecting cell lysis may include water or a solution having a solute (e.g., a salt such as NaCl) concentration of up to about 80 millimolar (for example, a 10-20 or 20-40 mM NaCl solution). Lysis can be effected, for example, at a temperature in the range of 20° C. to 40° C., preferably about 37° C. The tissue may be maintained in the hypotonic solution for about 4 hours to about 10 days, or preferably about 4 hours to about 8 hours. The amount of time needed to achieve cell lysis may depend on the temperature at which lysis is performed. For example, at higher temperatures, lysis may be achieved in a shorter period of time than when treated at a lower temperature.

D. Nuclease Treatment

The tissue is then contacted with a nuclease solution. For example, the issue may be incubated in a nuclease solution that is effective for degrading cellular nuclei material present in the tissue material. The nuclease solution may comprise one or more endonucleases such as Benzonase. The nuclease solution may comprise DNase and/or an RNase. In some embodiments, the tissue may be incubated in the nuclease solution at a temperature in the range of about 30° C. to about 40° C., preferably about 37° C. The tissue may be incubated in the nuclease solution for about 24 hours to about 30 hours or for any period of time sufficient to degrade the cell nuclei material.

In a preferred embodiment, the nuclease solution further comprises an antibacterial agent effective for preventing a bacterial bloom during nuclease treatment. For example, the nuclease solution may comprise one or more preservatives, antibiotics and/or antiseptic agents. Exemplary antibiotics include, but are not limited to, amikacin and levofloxacin. Exemplary preservatives include, but are not limited to, benzyl alcohol, sodium metabisulfite and/or methylparaben. Chlorhexidine is an exemplary antiseptic agent.

In some embodiments, the nuclease solution comprises about 0.8 to about 2.0% (v/v) benzyl alcohol. Benzyl alcohol is a bacteriostatic agent and has been discovered to be effective for preventing the growth of bacteria, particularly gram negative bacteria, during nuclease treatment. The nuclease treatment solution, without the benzyl alcohol, may provide conditions that allow for the growth of viable bacteria remaining from previous bioburden reduction treatments. Benzyl alcohol provides a bacteriostatic/bacteriocidal agent to the nuclease solution that does not negatively effect the process outcome.

In some embodiments, a nuclease treatment solution may comprise a DNase (e.g., DNase I), an RNase (e.g., RNase A), and benzyl alcohol. In some embodiments, the nuclease treatment solution comprises Benzonase. The nuclease treatment solution may further comprise $MgCl_2$, $CaCl_2$, and/or Tris-Cl. For example, the nuclease treatment solution may comprise about 48 mM Tris-Cl, about 2.88 mM $MgCl_2$, about 0.96 mM $CaCl_2$, about 19.2 µg/ml DNase I, and about 19.2 µg/ml RNase A in sterile water. In some embodiments, approximately 9 mL NF grade benzyl alcohol (98-100.5%) may be added per liter of nuclease solution to yield a final benzyl alcohol concentration of about 0.8 to about 2.0% (v/v).

E. Tissue Washout

After treatment with the nuclease-containing solution, the tissue may then be treated in an antibacterial/antifungal-containing buffer solution. In some embodiments, the solution may comprise one or more broad spectrum antibacterial agents and one or more antifungal agents in a physiological buffer in concentrations and/or amounts effective for reducing bioburden on the tissue material. For example, the solution may comprise an aminoglycoside, a betalactam and a polyene. In certain embodiments, the tissue may be treated with the antibacterial/antifungal-containing buffer solution for a period of about 24 to about 72 hours at a temperature between 2° C. and 40° C. In some embodiments, such as embodiments in which the tissue material is to be processed without contacting antibiotics, this step may be omitted.

F. Alkaline Alcohol Treatment

The tissue may then be treated in an alkaline alcohol solution. The alkaline alcohol solution may be effective for reducing the nuclease content of the tissue, reducing the viral load of the tissue and/or altering the textural quality of the tissue material. The alcohol component of the alkaline alcohol solution may comprise isopropanol, methanol or ethanol. The alkaline component of the alkaline alcohol solution may comprise a hydroxide salt. In some embodiments, the alkaline alcohol treatment solution may comprise ethanol in a concentration of about 72% to about 88% (v/v). In some embodiments, the alkaline solution may comprise about 0.016 M to about 0.022 M sodium hydroxide. In an exemplary embodiment, the alkaline alcohol solution comprises about 80% (v/v) ethanol and about 0.02 M sodium hydroxide in about 0.9% saline. The tissue may be treated in the alkaline alcohol solution for about 60 minutes to about 3 hours.

It has been discovered that treatment of the tissue with the alkaline alcohol solution may further reduce nuclease content of the tissue and reduces the viral load of the tissue. Thus, the alkaline alcohol treatment may increase the antiviral effectiveness of the process. Specifically, the alkaline alcohol treatment provides an independent viral inactivation modality distinct from that which is provided by terminal sterilization, e.g., irradiation. The alkaline alcohol may directly chemically interact with the virus particles, rendering the virus particles inactive. It has also been discovered that the treatment of the tissue with the alkaline alcohol solution beneficially imparts desirable textural qualities to the treated tissue and may allow the resulting tissue implant to be more easily handled by surgeons.

G. Chlorine Dioxide Treatment

The tissue may then be treated in a chlorine dioxide solution. The chlorine dioxide solution may comprise chlorine dioxide in sufficient concentration and/or amount to reduce the viral content of the tissue material. The tissue may be treated in a solution having a concentration of about 50 ppm or greater, on a continuous basis, for at least 60 minutes. Because the chlorine dioxide concentration may decrease during treatment by degradation, reaction or loss to the atmosphere, the initial concentration of the chlorine dioxide treatment solution may be greater than about 50 ppm of chlorine dioxide. In some embodiments, the chlorine dioxide solution may comprise about 100 to about 160 ppm chlorine dioxide. For example, the chlorine dioxide solution may comprise about 130 ppm chlorine dioxide in PBS at a refrigerated temperature. The tissue may be treated in the chlorine dioxide solution for one or more periods of about 60 to about 90 minutes. In certain embodiments, the tissue may be treated with the chlorine dioxide solution for two treatment periods, each treatment period lasting from about 60 to about 90 minutes.

It has been discovered that the addition of such a chlorine dioxide treatment to a treatment procedure that includes treatment with an alkaline alcohol solution and irradiation may advantageously result in ≥10 log virus reduction. In some embodiments, the chlorine dioxide gas may be generated at the point of use, e.g., it may be generated within the treatment solution. For example, the chlorine dioxide treatment solution may be produced by reacting sodium chlorite tablets with an organic acid in phosphate buffered saline (PBS).

H. Antioxidant Treatment

The tissue may then be treated with an antioxidant solution. The antioxidant solution may comprise an antioxidant in a sufficient quantity and/or concentration to degrade the chlorine dioxide remaining in the tissue material from a previous chlorine dioxide treatment step and/or to act as a radioprotectant for subsequent exposure to ionizing radiation. In some embodiments, the antioxidant solution may comprise ascorbic acid or one of its sodium, potassium, or calcium salts. In some embodiments, the antioxidant solution may comprise about 9.0 mM to about 11.0 mM of ascorbic acid or its salt in PBS. For example, the antioxidant solution may comprise about 9.0 mM to about 11.0 mM sodium ascorbate in PBS, or about 10.0 mM sodium ascorbate in PBS. The antioxidant may be in contact with the tissue at refrigerated temperatures, e.g., about 2° C. to about 10° C., over a period of about 16 to about 24 hours.

In some embodiments, other or additional antioxidants may be used. For example, butylhydroxytoluene and/or tocopherol may be used in place of sodium ascorbate or in combination with sodium ascorbate.

Advantageously, the tissue may be packaged in the antioxidant solution. The antioxidants in the solution may degrade the chlorine dioxide remaining in the tissue from the chlorine dioxide treatment, thereby reducing the toxicity of the implant or rendering the implant nontoxic. Because the high antioxidant concentration, the solution advantageously may also be radioprotective. That is, the antioxidant treatment solution may prevent oxidation and mitigate free radical damage from gamma irradiation.

I. Vacuum Sealing

The tissue may then be vacuum sealed to reduce further exposure of the tissue to oxygen. In some embodiments, the tissue is vacuum sealed in a package with the antioxidant treatment solution. Preferably, the tissue is vacuum sealed in package that is dimensioned to allow the tissue to be maintained in a flat and unfolded state when sealed. Various types of vacuum systems may be employed to create the seal. For example, a venturi or a vacuum pump may be used to remove air from the package prior to initiating a heat seal. In some embodiments, a vacuum level of about 13 in Hg is achieved before the heat seal is created. In some embodiments, an evacuate-flush-evacuate cycle is used to remove oxygen from the package. For example, the package may be subjected to a vacuum to evacuate the air from the package, then filled with an inert gas such as nitrogen or argon, and then subjected to a vacuum once again to evacuate the inert gas (e.g., nitrogen or argon) from the package.

The removal of air from the package prevents air pockets from developing between the tissue implant and the pouch and reduces free radical formation when then package is subjected to gamma irradiation. The vacuum also advantageously causes the package to maintain the tissue in a flat and stationary position during transport and prevents the formation of permanent folds/creases when the tissue is subjected to irradiation.

J. Packaging of Tissue for Transport

The tissue may thereafter packaged for transport. In some embodiments, a double pouch configuration is employed. The vacuum sealed inner pouch may comprise a clear film material. For example, the inner pouch may be formed of a multilayer laminate film with an inner heat-sealable layer and one or more outer layers having good oxygen barrier properties. The inner pouch may have a low vapor transmission level. In some embodiments, the heat sealed inner pouch is stored in an outer pouch, which may comprise foil or a metalized polymer film. The outer pouch preferably does not allow for any measureable vapor transmission. The double pouch configuration may have a shelf life of at least two years under ambient conditions. Advantageously, the tissue may be stored without refrigeration or freezing. The packaging, e.g., the inner pouch and outer pouch, is preferably radiation stable.

In some embodiments, the tissue is transported cold but at a temperature greater than the freezing point of the antioxidant treatment solution so that the tissue is not allowed to freeze during transport.

K. Sterilization/Crosslinking

The tissue may be terminally sterilized while packaged. In some embodiments, the tissue implant is subjected to gamma or electron beam irradiation in a radiation dosage sufficient to further reduce the microbial content of the tissue material. For example, the tissue may be subjected to radiation of about 15 to about 40 kGy. In some embodiments, the tissue implant is sterilized with a radiation dosage sufficient to achieve a Sterility Assurance Level (SAL) of 10 to the minus 6.

In other embodiments, the tissue may be terminally sterilized with chemical sterilants or may be treated with crosslinking agents or other chemicals prior to or after packaging. In some embodiments, the tissue implant is contacted with the chemicals in sufficient concentration and/or amount to further reduce the microbial content of the tissue material. For example, the tissue mat be treated with ethylene oxide, formaldehyde, peracetic acid, hydrogen peroxide, ozone, glutaraldehyde, propiolactone, o-phthaldehyde, propylene oxide, mercurials, phenols, chlorine, hypochlorite, iodophore, peracetic acid, superoxidized water, chlorhexidine, detergents, supercritical fluids (e.g., supercritical $CO_2$), quaternary ammonium compounds, silver, kathon, inactine (PEN110), ultrasonication, pressure cycling, and/or steam.

L. Unpackage and Use

Immediately prior to use, the tissue may be removed from the packaging by peeling away, tearing, or cutting the outer pouch and inner pouch. In embodiments in which the tissue is stored in the antioxidant treatment solution, the tissue is ready for use when removed from the inner pouch without requiring rinsing or re-hydration.

The tissue may then be implanted at the desired location. For example, the tissue implant may be used to reinforce soft tissues where weakness exists. In some embodiments, the tissue may be used to reinforce soft tissues repaired by sutures or by suture anchors, e.g., as part of a tendon repair surgery. In some embodiments, the tissue is implanted as a patch to repair defects of the abdominal or thoracic wall. The tissue implant may also be implanted in patch form to repair the heart, a rectal or a vaginal prolapse, or it may be implanted for reconstruction of the pelvic floor. The tissue may be implanted to patch hernias, as a reinforcement for a suture-line, or it may be used in breast or other reconstructive and/or cosmetic procedures. The tissue implant may be utilized as a vascular patch as in the procedure of endaterectomy. The tissue implant may also be used in urinary systems. In some embodiments, the tissue is implanted as to reinforce a rotator cuff, a patella, an Achilles, a bicep, a quadriceps, or other tendon or ligament.

II. Tissue Implants

Tissue implants produced by the foregoing methods may possess many desirable properties for reconstructive and reinforcing applications, such as suitable mechanical strength, biocompatibility, and the ability to support recellularization in vivo. The tissue implants may further provide good physical support for repair, and a biological scaffold for healing.

In some embodiments, the tissue implants are essentially acellular. In certain embodiments, the tissue implants have at least 95% fewer intact cells, or 99% fewer intact cells than the naturally occurring biological material. In some embodiments, the tissue implants consist essentially of structural proteins, e.g., collagen and elastin. In some embodiments, the tissue implants are unfixed, i.e., not chemically cross-linked. The tissue may also be cross-linked, such as with 1-ethyl-3-(3-dimethylaminopropyl)carbodiimide ("EDC"). The tissue implants may therefore be remodelable. The tissue implants may also support healing by providing a tissue matrix that is capable of recellularizing and remodeling.

In some embodiments, the tissue implant may comprise decellularized tissue, such as decellularized human, bovine, equine, macropodidae or porcine pericardium, dermis, omentum, amniotic membrane, peritoneum, or urinary bladder. The tissue implants may also comprise decellularized tissue materials of other origins, including vascular tissues, orthopedic tissues, connective tissues, cardiac tissues, and other tissues that are sheet-like in configuration.

The tissue implants may be of uniform thickness and physical properties. For example, the tissue implant may be a patch, such as a patch in the shape of a circle, ellipse, oval, or rectangle. In a preferred embodiment, the tissue implant may be a patch that is substantially circular shape, for example, a circle having a diameter of about 4 cm to about 12 cm, or more preferably about 5 cm to about 10 cm, or about 7 cm. In another embodiment, the tissue implant may be in the form of a patch that is substantially elliptical in shape, such as a 5 cm by 8 cm ellipse. The tissue implant may be formed into a patch of various other shapes including regular and irregular polygons, curvilinear shapes, and combinations thereof.

Tissue implants produced by the foregoing methods have been tested in accordance with standardized testing methodologies (e.g., ISO 10993) and have been found to be non-cytotoxic, non-sensitizing, non-irritating, non-genotoxic, non-pyrogenic, non-hemolytic, and do not promote system toxicity (See TABLE 1).

TABLE 1

Tissue Implant Test Methodologies and Outcomes

| Test Methodology | Outcome |
| --- | --- |
| Cytotoxicity<br>ISO Elution Method, 1X MEM Extract | Not cytotoxic |
| Sensitization<br>ISO Maximization Sensitization: 0.9% saline and vegetable oil extracts | Not sensitizing |
| Irritation<br>ISO Intracutaneous Study: 0.9% saline and vegetable oil extracts | Not irritating |
| Systemic Toxicity<br>USP & ISO 0.9% saline and vegetable oil extracts | No systemic toxicity |
| Genotoxicity<br>Bacterial Reverse Mutation, in vitro Mammalian cells,<br>Mouse Peripheral Blood Micronucleus | Not genotoxic |

TABLE 1-continued

Tissue Implant Test Methodologies and Outcomes

| Test Methodology | Outcome |
|---|---|
| Pyrogenicity Material Mediated –0.9% SC Extract | Non-pyrogenic |
| In Vitro Hemolysis Whole rabbit blood lysis - ASTM | Not hemolytic |

Biomechanical evaluations of the tissue implants have demonstrated high tensile, burst, and tear resistance, as well as suitable suture retention strengths. The denaturation temperatures of tissue implants produced by the foregoing methods are consistent with decellularized and irradiated connective tissue matrices. In some embodiments, the tissue implants are also ready to use directly out of the package and do not require rehydration or rinsing.

The tissue implants produced by the foregoing methods are also terminally sterile and essentially virus free. The tissue implants have a Sterility Assurance Level (SAL) of better than $10^{-6}$, which indicates that the present method yields a greater than 6 log reduction in microbial organisms. The tissue implants may exhibit at least 10 log viral reduction.

EXAMPLE

In pilot production studies, it was discovered that there is a potential for growth of gram-negative bacteria during nuclease treatment. It is believed that the environmental conditions present during nuclease treatment, e.g., temperature, moisture and available food source, favors the growth of gram-negative bacteria.

Selection of Nuclease Treatment Additives

From extensive literature review, a combination of amikacin and levofloxacin was hypothesized to provide the required antibacterial coverage. The concentration for both antibiotics was chosen as the approximate middle of the minimum inhibitory concentration against sensitive bacteria (MIC) range (levofloxacin 0.03-32 µg/mL and amikacin 0.125-32 µg/mL) or 16 µg/mL.

For non-antibiotic alternatives, benzyl alcohol, sodium metabisulfite and methylparaben were also selected from an extensive list of chemical preservatives and disinfectants for consideration. For the initial evaluation additions of 0.9% benzyl alcohol and 0.2% sodium metabisulfite were used. The chemical disinfectant chlorhexidine was selected for use in the form of chlorhexidine gluconate at the concentration of 0.12%.

An acidic nuclease formulation having a pH of 5.0 was prepared by substituting the Tris-Cl buffer system with a 0.1 M sodium acetate buffering system. The slightly acidic pH is below the minimum for favorable growth of the *Pseudomonas* sp. Since the pH is not optimal for the functionality of the nuclease, the concentrations of $CaCl_2$ and $MgCl_2$ in the solution were increased to 10 mM in an attempt to offset any loss in activity.

Experimental Method

The evaluation of the nuclease solution variations had two components, an assessment of the effect on the enzymatic activity level of the DNase and RNase, and an assessment effect on bacteria growth. A 400 ml volume of each nuclease solution was formulated, including:
  Standard nuclease (N).
  Standard nuclease+16 µg/mL levofloxacin and 16 µg/mL Amikacin ($N_A$)
  Standard nuclease+0.9% benzyl alcohol ($N_{p1}$)
  Standard nuclease+0.2% sodium metabisulfite ($N_{p2}$).
  Standard nuclease+0.12% chlorhexidine gluconate ($N_{p3}$)
  Acidic nuclease ($N_{pH}$)

For the enzymatic activity assessment, a sample of each solution as first analyzed for RNase and DNase enzymatic activity. The results of the analysis were used to determine if any of the nuclease variations should be removed from further evaluation.

To assess the effect on bacterial growth the nuclease solutions was evaluated with a pericardium tissue process model. For each solution, a sheet (10 cm×20 cm) of bovine pericardium that had been processed through the bioburden reduction and hypotonic lysis treatment was cut into two sections (10 cm×10 cm).

One of the two sections was placed into a container with 100 mL of a nuclease solution. The second section was placed into a container and inoculated with 1 mL of *Stenotrophomonas maltophllia* ("SMAL") at 100-1000 cfu/mL. The tissue was left undisturbed for a 15 minute adhesion interval at room temperature. 100 mL of the nuclease solution was then added to the container. The tissues were incubated for 24-30 hours to simulate the standard nuclease treatment. Following the incubation period, each tissue was transferred to a container with 100 mL of sterile PBS for a rinse recovery assay to determine the bioburden load. The rinse recovery solutions were diluted and filter plated to Tryptic Soy Agar ("TSA"), incubated at 30-35° C. and evaluated for countable colonies.

Results

Results of the enzyme activity assay indicated a reduction in the DNase activity from the acidic nuclease solution, and the results of the RNase activity were inconclusive. The results of the activity assays on the benzyl alcohol, sodium metabisulfite, and chlorhexidine gluconate indicated no change in the DNase and RNase activity as compared to the control solutions. Considering these results the acidic nuclease was removed from further evaluation.

To reduce the size of the evaluation, the additives evaluated were limited to the antibiotics, chlorhexidine gluconate and the benzyl alcohol. The count plates had an average of 45 colonies at a $10^{-1}$ dilution or 450 colonies/mL. The calculated microbial bioburden from the inoculated tissues were 450 cfu for the control and no visible colonies for the three additive solutions. The calculated microbial bioburden from the tissues without the inoculation were 1090 cfu for the control and 35, 0 and 0 for the antibiotics, benzyl alcohol and chlorhexidine gluconate, respectively.

These results indicate all three solutions were minimally capable of preserving the original bioburden level, and in general reduced the bioburden by 2-3 logs (See TABLES 2 and 3).

TABLE 2

Results of Nuclease Additive Effectiveness as a Preservative with Processed Bovine Pericardium (Natural Flora)

| Microorganism | Natural Flora | | | | | | | |
|---|---|---|---|---|---|---|---|---|
| Dilution | 10 mL | 1 mL | $10^{-1}$ mL | $10^{-2}$ mL | $10^{-3}$ mL | $10^{-4}$ mL | $10^{-6}$ mL | $10^{-6}$ mL |
| Multiplier | 1.00E+01 | 1.00E+02 | 1.00E+03 | 1.00E+04 | 1.00E+05 | 1.00E+06 | 1.00E+07 | 1.00E+07 |

TABLE 2-continued

Results of Nuclease Additive Effectiveness as a Preservative with Processed Bovine Pericardium (Natural Flora)

| Microorganism | Natural Flora | | | | | | | |
|---|---|---|---|---|---|---|---|---|
| Nuclease | 112 | 9 | 2 | 0 | 0 | 0 | 0 | 0 |
| Nuclease | 106 | 20 | 1 | 0 | 0 | 0 | 0 | 0 |
| Average Count | 109 | 15 | 2 | 0 | 0 | 0 | 0 | 0 |
| Results | 1090 | 1450 | 1500 | 0.00E+00 | 0.00E+00 | 0.00E+00 | 0.00E+00 | 0.00E+00 |
| Nuclease + Antibiotics | 3 | 1 | 0 | 0 | 0 | 0 | 0 | 0 |
| Nuclease + Antibiotics | 4 | 0 | 0 | 0 | 0 | 0 | 0 | 0 |
| Average Count | 4 | 1 | 0 | 0 | 0 | 0 | 0 | 0 |
| Results | 35 | 50 | 0 | 0.00E+00 | 0.00E+00 | 0.00E+00 | 0.00E+00 | 0.00E+00 |
| Nuclease + Benzyl Alcohol | 0 | 0 | 0 | 0 | 0 | 0 | 0 | 0 |
| Nuclease + Benzyl Alcohol | 0 | 0 | 0 | 0 | 0 | 0 | 0 | 0 |
| Average Count | 0 | 0 | 0 | 0 | 0 | 0 | 0 | 0 |
| Results | 0.00E+00 | 0.00E+00 | 0.00E+00 | 0.00E+00 | 0.00E+00 | 0.00E+00 | 0.00E+00 | 0.00E+00 |
| Nuclease + Chlorhexidine | 0 | 0 | 0 | 0 | 0 | 0 | 0 | 0 |
| Nuclease + Chlorhexidine | 0 | 0 | 0 | 0 | 0 | 0 | 0 | 0 |
| Average Count | 0 | 0 | 0 | 0 | 0 | 0 | 0 | 0 |
| Results | 0.00E+00 | 0.00E+00 | 0.00E+00 | 0.00E+00 | 0.00E+00 | 0.00E+00 | 0.00E+00 | 0.00E+00 |

TABLE 3

Results of Nuclease Additive Effectiveness as a Preservative with Processed Bovine Pericardium (Spiked with SMAL)

| Microorganism | SMAL | | | | | | | |
|---|---|---|---|---|---|---|---|---|
| Dilution | 10 mL | 1 mL | $10^{-1}$ mL | $10^{-2}$ mL | $10^{-3}$ mL | $10^{-4}$ mL | $10^{-6}$ mL | $10^{-6}$ mL |
| Multiplier | 1.00E+01 | 1.00E+02 | 1.00E+03 | 1.00E+04 | 1.00E+05 | 1.00E+06 | 1.00E+07 | 1.00E+07 |
| Nuclease | 36 | 2 | 0 | 0 | 0 | 0 | 0 | 0 |
| Nuclease | 53 | 5 | 0 | 0 | 0 | 0 | 0 | 0 |
| Average Count | 45 | 4 | 0 | 0 | 0 | 0 | 0 | 0 |
| Results | 4.45E+02 | 3.50E+02 | 0.00E+00 | 0.00E+00 | 0.00E+00 | 0.00E+00 | 0.00E+00 | 0.00E+00 |
| Nuclease + Antibiotics | 0 | 0 | 0 | 0 | 0 | 0 | 0 | 0 |
| Nuclease + Antibiotics | 0 | 0 | 0 | 0 | 0 | 0 | 0 | 1 |
| Average Count | 0 | 0 | 0 | 0 | 0 | 0 | 0 | 1 |
| Results | 0.00E+00 | 0.00E+00 | 0.00E+00 | 0.00E+00 | 0.00E+00 | 0.00E+00 | 0.00E+00 | 5.00E+06 |
| Nuclease + Benzyl Alcohol | 0 | 0 | 0 | 0 | 0 | 0 | 0 | 0 |
| Nuclease + Benzyl Alcohol | 1 | 1 | 0 | 0 | 0 | 0 | 0 | 0 |
| Average Count | 1 | 1 | 0 | 0 | 0 | 0 | 0 | 0 |
| Results | 1.00E+00 | 1.00E+00 | 0.00E+00 | 0.00E+00 | 0.00E+00 | 0.00E+00 | 0.00E+00 | 0.00E+00 |
| Nuclease + Chlorhexidine | 0 | 0 | 0 | 1 | 0 | 0 | 0 | 0 |
| Nuclease + Chlorhexidine | 0 | 0 | 0 | 0 | 0 | 0 | 0 | 0 |
| Average Count | 0 | 0 | 0 | 1 | 0 | 0 | 0 | 0 |
| Results | 0.00E+00 | 0.00E+00 | 0.00E+00 | 0.00E+00 | 0.00E+00 | 0.00E+00 | 0.00E+00 | 0.00E+00 |

Modifications and variations of the methods, products, and systems described herein will be obvious to those skilled in the art from the foregoing detailed description. Such modifications and variations are intended to come within the scope of the appended claims.

We claim:

1. A method of preparing a tissue implant for implantation comprising:
    treating a decellularized tissue material with an alkaline alcohol solution comprising an alkaline component in an amount from about 0.016 M to about 0.022 M, wherein the tissue material comprises mammalian pericardium.

2. The method of claim 1, wherein the alkaline alcohol solution comprises ethanol.

3. The method of claim 2, wherein the ethanol is present in a concentration of about 72 to about 88 percent v/v.

4. The method of claim 1, wherein the alkaline component comprises a hydroxide salt.

5. The method of claim 4, wherein the hydroxide salt comprises sodium hydroxide.

6. The method of claim 5, wherein the alkaline alcohol solution is about 0.020 M sodium hydroxide.

7. The method of claim 1, wherein the alkaline alcohol solution comprises ethanol in a concentration from about 72 to about 88 percent v/v and about 0.016 M to about 0.022 M sodium hydroxide.

8. The method of claim 1, wherein the decellularized tissue material is treated with the alkaline alcohol solution for about 60 minutes to about 3 hours.

9. The method of claim 1, wherein the decellularized tissue material comprises human, bovine, porcine, or equine pericardium.

10. A method of preparing a tissue implant for implantation comprising:
   treating a decellularized tissue material with an alkaline alcohol solution comprising an alkaline component in an amount from about 0.016 M to about 0.022 M; and thereafter
   treating the decellularized tissue material with a chlorine dioxide solution.

11. The method of claim 10, wherein the alkaline alcohol solution comprises ethanol.

12. The method of claim 11, wherein the ethanol is present in a concentration of about 72 to about 88 percent v/v.

13. The method of claim 10, wherein the alkaline component comprises sodium hydroxide.

14. The method of claim 13, wherein the alkaline alcohol solution is about 0.02 M sodium hydroxide.

15. The method of claim 10, wherein the alkaline alcohol solution comprises ethanol in a concentration from about 72 to about 88 percent v/v and about 0.016 M to about 0.022 M sodium hydroxide.

16. The method of claim 10, wherein the decellularized tissue material is treated with the alkaline alcohol solution for about 60 minutes to about 3 hours.

17. The method of claim 10, wherein during the treatment with the chlorine dioxide treatment solution, the chlorine dioxide treatment solution comprises greater than about 50 ppm chlorine dioxide for about 60 minutes or longer.

18. A method of preparing a tissue implant for implantation comprising:
   treating a decellularized tissue material with an alkaline alcohol solution comprising sodium hydroxide and ethanol, wherein the ethanol is present in the alkaline alcohol solution in a concentration from about 72 to about 88 percent v/v and the alkaline alcohol solution comprises about 0.016 M to about 0.022 M sodium hydroxide.

19. The method of claim 18, wherein the decellularized tissue material comprises human, bovine, porcine, or equine pericardium.

20. A method of preparing a tissue implant for implantation comprising:
   treating a decellularized tissue material with an alkaline alcohol solution comprising from about 0.016 M to about 0.022 sodium hydroxide and ethanol for about 60 minutes to about 3 hours; and thereafter
   treating the decellularized tissue material with a chlorine dioxide solution comprising greater than about 50 ppm chlorine dioxide for about 60 minutes or longer;
   wherein the decellularized tissue material comprises mammalian pericardium.

* * * * *